(12) United States Patent
Norris et al.

(10) Patent No.: US 7,921,678 B2
(45) Date of Patent: Apr. 12, 2011

(54) COMPRESSIBLE RESILIENT FABRIC, DEVICES, AND METHODS

(75) Inventors: Stephanie Booz Norris, Rocky Point, NC (US); Martin Monestere, Jr., Hollywood, SC (US); Brian L. McMurray, Pinehurst, NC (US)

(73) Assignee: Atex Technologies, Inc., Pinebluff, NC (US)

( * ) Notice: Subject to any disclaimer, the term of this patent is extended or adjusted under 35 U.S.C. 154(b) by 46 days.

(21) Appl. No.: 12/143,442

(22) Filed: Jun. 20, 2008

(65) Prior Publication Data

US 2008/0319521 A1    Dec. 25, 2008

Related U.S. Application Data (60) Provisional application No. 60/936,405, filed on Jun. 20, 2007.

(51) Int. Cl.
*D04B 1/22* (2006.01)
(52) U.S. Cl. ........................................................ 66/195
(58) Field of Classification Search .................. 66/202, 66/191, 194; 623/1.49–1.54
See application file for complete search history.

(56) References Cited

U.S. PATENT DOCUMENTS

| | | | | |
|---|---|---|---|---|
| 3,655,474 A | * | 4/1972 | Constantine | 156/178 |
| 3,878,565 A | * | 4/1975 | Sauvage | 623/1.5 |
| 4,047,252 A | * | 9/1977 | Liebig et al. | 623/1.52 |
| 4,193,137 A | * | 3/1980 | Heck | 623/1.52 |
| 4,567,075 A | * | 1/1986 | Krawczyk | 428/91 |
| 4,892,539 A | * | 1/1990 | Koch | 623/1.52 |
| 5,292,328 A | * | 3/1994 | Hain et al. | 606/151 |
| 5,611,127 A | | 3/1997 | Ceriani et al. | |

(Continued)

FOREIGN PATENT DOCUMENTS

EP    08768655.6    2/2010

(Continued)

OTHER PUBLICATIONS

International Search Report, PCT/US02/007684, mailed Jan. 28, 2009.

(Continued)

*Primary Examiner* — Danny Worrell
(74) *Attorney, Agent, or Firm* — Boggs IP Law, LLC (57) ABSTRACT

A compressible resilient fabric can include a ground layer of knitted yarn, and a loop layer comprising a plurality of loops of yarn, each loop having a point knit into the ground layer. The fabric can be compressible from an non-compressed configuration, in which each loop has an apex extending substantially perpendicularly outward from the ground layer, into a compressed configuration, in which each loop is collapsed onto the ground layer. The fabric can further be resilient so as to substantially resume the non-compressed configuration when compression is relieved. The loop layer yarn can include a multifilament yarn having a high denier per filament ratio. The ground layer yarn can include a yarn shrinkable substantially more than the loop layer yarn. The loops can be densely knit so as to support the extension of the loops outward from the ground layer.

11 Claims, 2 Drawing Sheets

U.S. PATENT DOCUMENTS

| | | | |
|---|---|---|---|
| 5,732,572 A * | 3/1998 | Litton | 66/195 |
| 6,015,431 A | 1/2000 | Thornton et al. | |
| 6,221,099 B1 * | 4/2001 | Andersen et al. | 623/1.15 |
| 6,547,820 B1 * | 4/2003 | Staudenmeier | 623/1.49 |
| 6,663,667 B2 * | 12/2003 | Dehdashtian et al. | 623/1.51 |
| 6,783,554 B2 * | 8/2004 | Amara et al. | 623/23.76 |
| 6,994,722 B2 | 2/2006 | DiCarlo | |
| 2001/0056303 A1 * | 12/2001 | Caneiro et al. | 623/23.74 |
| 2002/0116070 A1 * | 8/2002 | Amara et al. | 623/23.74 |
| 2003/0028239 A1 | 2/2003 | Dong | |
| 2004/0054376 A1 * | 3/2004 | Ory et al. | 606/151 |
| 2004/0243221 A1 | 12/2004 | Fawzi et al. | |

FOREIGN PATENT DOCUMENTS

| | | |
|---|---|---|
| EP | 08768655.6 | 3/2010 |
| WO | WO 02/28314 | 4/2002 |

OTHER PUBLICATIONS

Written Opinion of the International Searching Authority, PCT/US02/007684, mailed Jan. 28, 2009.

* cited by examiner

Stitch Notation:

Bar 1: 1-0 / 0-0 / 0-0 / 1-1 //
Bar 2: 1-1 / 0-0 / 0-1 / 1-1 //
Bar 3: 1-0 / 1-1 / 1-2 / 1-1 //
Bar 4: 2-3 / 2-2 / 1-0 / 2-2 //

Fig. 5

COMPRESSIBLE RESILIENT FABRIC, DEVICES, AND METHODS

CROSS-REFERENCE TO RELATED APPLICATIONS

This application claims benefit of U.S. Provisional Patent App. No. 60/936,405, filed Jun. 20, 2007, which is incorporated by reference herein in its entirety.

FIELD OF THE INVENTION

The present invention relates to compressible resilient fabric, devices including a compressible resilient fabric, and methods for making and/or using a compressible resilient fabric and/or device having a compressible resilient fabric.

BACKGROUND

Medical devices such as vascular and endovascular grafts and stent-grafts can include fabric components that function to promote sealing of the device to the lumen or structure in which it is implanted. Insertion of such devices and fabric components into target sites can require that the fabric be compressed and collapsed so as to be placed inside a delivery catheter or cannula. When such a device having a fabric component is inserted to a target site and the delivery catheter is removed, at least the fabric component is often expected to rebound to approximately its original shape, structure, and dimensions. Regaining its original shape, structure, and dimensions is important to achieve an adequate seal between the exterior of the device and the lumen or structure in which it is implanted. This is critical because any gaps or voids between the device and the implant site can prevent a reliable seal, which can lead to complications and/or device failure. The ability of such a fabric component to regain its original shape, structure, and dimensions after being compressed and implanted can often depend on the fabric having sufficient resiliency.

In some applications, medical devices comprising fabric and designed for insertion into vessels or ducts may be stored in a compressed, or collapsed, configuration for extended periods, for example, a number of months, before use. When stored in sterile packaging, such devices are secluded from exposure to ambient air. In such devices stored for prolonged periods in a compressed state and without exposure to ambient air, recovery of fabric to its original shape and dimensions can be adversely affected. In addition, some implantable medical devices can be stored in fluid media over various periods of time. Fabric components of such medical devices can absorb fluid media in which they are packaged and stored. When medical device fabric absorbs fluid media, the fabric may be lose some resiliency for regaining its original shape and dimensions when deployed.

Thus, there is a need for a fabric that can be compressed for ease of delivery to an implant site and that has sufficient resiliency to regain its original shape, structure, and dimensions when implanted. There is a need for such a fabric that can avoid the loss of performance characteristics during storage prior to use.

SUMMARY

The present invention can include embodiments of a compressible resilient fabric, devices including a compressible resilient fabric, and methods for making and/or using a fabric and/or device having a compressible resilient fabric.

In an illustrative embodiment, a compressible resilient fabric can include a ground layer of knitted yarn, and a loop layer comprising a plurality of loops of yarn, each loop having a point knit into the ground layer. The fabric can be compressible from a non-compressed configuration, in which each loop has an apex extending substantially perpendicularly outward from the ground layer, into a compressed configuration, in which each loop is collapsed onto the ground layer. The fabric can be resilient so as to substantially resume the non-compressed configuration when compression is relieved.

In some embodiments, the loop layer yarn can comprise a multifilament yarn having a high denier per filament ratio. For example, the loop layer yarn can comprise a multifilament yarn having 5-20 denier per filament. In some embodiments, the loop layer yarn can comprise a total denier of 60-70. In some embodiments, the ground layer yarn can comprise a yarn shrinkable substantially more than the loop layer yarn. For example, the ground layer yarn may comprise a yarn shrinkable about 40-60%, and the loop layer yarn can comprise a yarn shrinkable about 7-8%. In some embodiments, the loops can be densely knit so as to support the extension of the loops outward from the ground layer.

Some embodiments of the present invention can include a device comprising a substantially tubular inner member, and an intraluminal sealing member attachable to an exterior of the inner member. The sealing member can include a ground layer of knitted yarn and a loop layer comprising a plurality of loops of yarn, each loop having a point knit into the ground layer. The sealing member can be compressible from an non-compressed configuration, in which each loop has an apex extending substantially perpendicularly and radially outward from the ground layer, into a compressed configuration, in which each loop is collapsed onto the ground layer. The sealing member can further be resilient so as to substantially resume the non-compressed configuration when compression is relieved, for example, after the device is implanted into a lumen in a human or animal body. The intraluminal sealing member can be adapted to promote sealing between the inner member and a lumen wall. In some embodiments, the inner member can comprise a stent.

Some embodiments of the present invention can include a system and/or kit. Such a system and/or kit can include a compressible resilient fabric and/or devices including a compressible resilient fabric as described herein.

Some embodiments of the present invention can include a method of making a compressible resilient fabric and/or devices including a compressible resilient fabric. Such a method can include knitting a ground layer of yarn and a loop layer comprising a plurality of loops of yarn, each loop having a point knit into the ground layer. The method can further include washing the fabric in about 90 degree C. water. The method can further include drying the fabric at about 60-65 degrees C., which further shrinks the fabric. In the fabric and/or device made by such a method, the fabric can be compressible from a non-compressed configuration, in which each loop has an apex extending substantially perpendicularly outward from the ground layer, into a compressed configuration, in which each loop is collapsed onto the ground layer. The fabric can further be resilient so as to substantially resume the non-compressed configuration when compression is relieved.

Features of a fabric, device, system, kit, and/or method of the present invention may be accomplished singularly, or in combination, in one or more of the embodiments of the present invention. As will be realized by those of skill in the art, many different embodiments of a fabric, device, system, kit, and/or method according to the present invention are possible. Additional uses, advantages, and features of the invention are set forth in the illustrative embodiments discussed in the detailed description herein and will become more apparent to those skilled in the art upon examination of the following.

DETAILED DESCRIPTION

For the purposes of this specification, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the embodiments described herein. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the described embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, for example, 5.5 to 10. Additionally, any reference referred to as being "incorporated herein" is to be understood as being incorporated in its entirety.

For the purposes of this specification, terms such as "forward," "rearward," "front," "back," "right," "left," "upwardly," "downwardly," and the like are words of convenience and are not to be construed as limiting terms. As used in this specification and the appended claims, the singular forms "a," "an," and "the" include plural referents unless the context clearly dictates otherwise. Thus, for example, the term "a loop" is intended to mean a single loop or more than one loop.

The present invention can include embodiments of a compressible resilient fabric, devices including a compressible resilient fabric, and methods for making and/or using a fabric and/or device comprising a compressible resilient fabric. Some embodiments of compressible resilient fabrics, devices, and methods according to the present invention may be useful for medical applications, for example, a stent comprising an intraluminal sealing member.

For purposes herein, "compressible" is defined as the ability of the fabric or intraluminal sealing member to be compressed from a relatively larger, expanded configuration to a relatively smaller, compressed configuration. For example, the fabric and/or intraluminal sealing member can be compressed from its original non-compressed configuration to the compressed configuration. In some embodiments, the entire dimension of the fabric along its length and width can be compressed. For purposes herein, "resilient" is defined as the ability of the fabric or intraluminal sealing member to recover from the compressed configuration to substantially its original shape, structure, and dimensions as in the non-compressed configuration.

Figure 1:
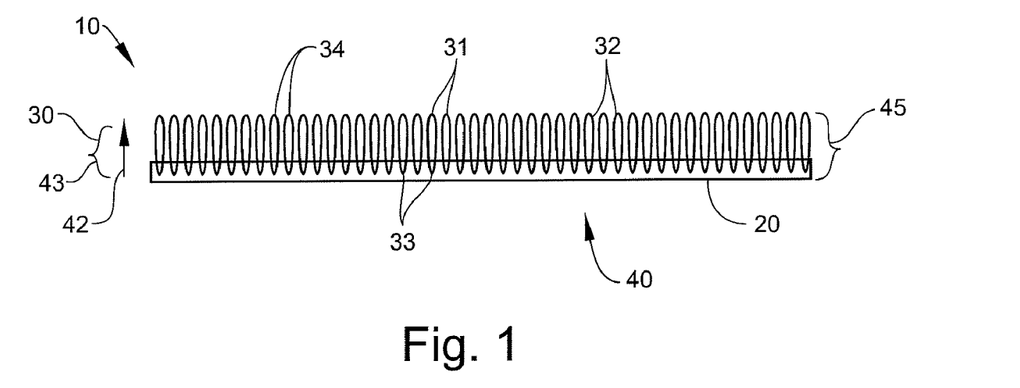
FIG. 1 is a diagrammatic side view of a compressible resilient fabric in a non-compressed configuration in an embodiment of the present invention.
Figure 2:
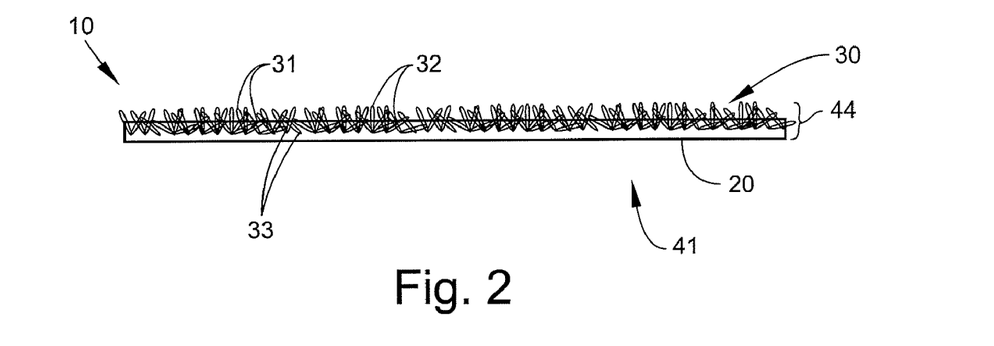
FIG. 2 is a diagrammatic side view of the compressible resilient fabric shown in FIG. 1, showing the loops compressed into the ground layer in a compressed configuration.
Figure 3:
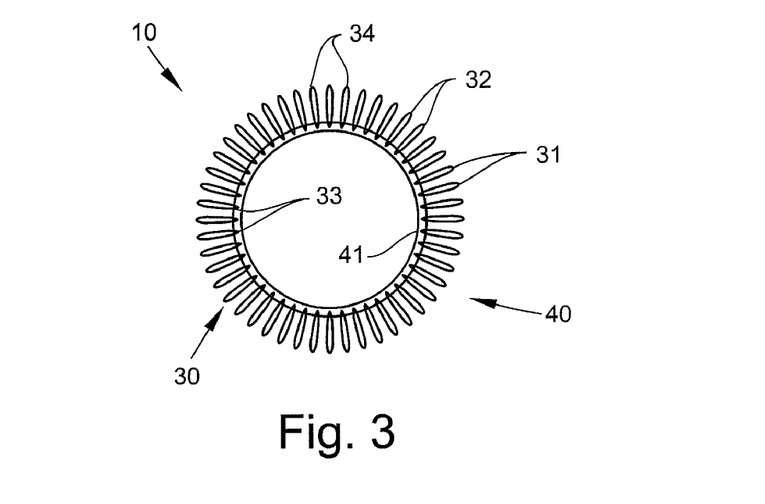
FIG. 3 is a diagrammatic cross-sectional view of a tubular-shaped compressible resilient fabric in a non-compressed configuration in an embodiment of the present invention.

In an illustrative embodiment, as shown in FIGS. 1-3, a compressible resilient fabric 10 can include a ground layer 20 of knitted yarn, and a loop layer 30 comprising a plurality of loops 32 of yarn 31, each loop 32 having a point 33 knit into the ground layer 20. The fabric 10 can be compressible from a non-compressed configuration 40, in which each loop 32 has an apex 34 extending substantially perpendicularly outward 42 from the ground layer 20, into a compressed configuration 41, in which each loop 32 is collapsed onto the ground layer 20. The fabric 10 can be sufficiently resilient so as to substantially resume the non-compressed configuration 40 when compression is relieved.

In some embodiments, the loop layer yarn 31 can comprise a multifilament yarn 31 having a high denier per filament ratio. For example, the loop layer yarn 31 can comprise a multifilament yarn 31 having 5-20 denier per filament. In some embodiments, the loop layer yarn can comprise a total denier of 60-70.

In some embodiments, the ground layer yarn can comprise a yarn substantially more shrinkable than the loop layer yarn 31. For example, the ground layer yarn may comprise a yarn shrinkable about 40-60%, and the loop layer yarn 31 can comprise a yarn 31 shrinkable about 7-8%.

In some embodiments, the loops 32 can be densely knit so as to support the extension of the loops 32 outward from the ground layer 20. For example, in certain embodiments, the loop layer 30 can include two loops 32 in every four courses of the ground layer 20. In particular embodiments, the loop layer 30 can include between about 600 and about 750 loops 32 per square inch of the fabric 10. In some embodiments, each loop 32 can have a substantially uniform height 43 in the non-compressed configuration 40.

In the non-compressed configuration 40, some embodiments of the fabric 10 can have a thickness 43 of about 1-5 mm. In the compressed configuration 41, some embodiments of the fabric 10 can have a thickness 44 of about 0.004-0.008 inches. Thus, some embodiments of the fabric 10 can be compressed into a very thin profile for insertion to a target site in a location in a body, and recover to substantially its original non-compressed configuration 40 when positioned in the location and compression is relieved.

In some embodiments, the loops 32 can be constructed as "unitary" with the ground layer 20. A "unitary" construction means that loops 32 are knit in a set repeat pattern so as to provide a uniform density. With a uniform density, gaps and voids in the knit pattern can be avoided. In some embodiments, the loops 32 can be constructed as "integral" with the ground layer 20. An "integral" construction means that the loops 32 are knit simultaneously with and into the ground layer 20. In some embodiments, the apex 34 of the loops 32 can be substantially erect, or perpendicular 42 to the face side, or technical face, of the ground layer 20 of the fabric 10.

The fabric 10 may be compressed from its original non-compressed configuration 40 into the smaller, compressed configuration 41 by employing, for example, a mechanical crimping apparatus (not shown) designed for reducing the overall size of an intraluminal medical device 50. Once crimped to the smaller size, the fabric 10 (and device) can be loaded into a delivery catheter. When a compressive pressure, such as the wall of a delivery catheter, is removed from the compressible resilient fabric 10 and/or medical device 50 comprising the fabric 10, the fabric 10 can recover from the compressed configuration 41 to substantially its original non-compressed, or expanded, configuration 40. Such recovery to substantially the original non-compressed configuration 40 can include return of the loops 32 to approximately the original, non-compressed loop, or pile, height 43 and other dimensions and shape.

Such self-recovery can be facilitated by various aspects of the present invention, as described herein. For example, in some embodiments, resilient recovery of the loops 32 to the non-compressed configuration 40, including their non-compressed loop height 43, can be provided at least in part by loop yarns 31 having higher denier per filament and relatively fewer filaments of yarn 31. In some embodiments, resilient recovery of the loops 32 to the non-compressed configuration 40 can be provided at least in part by the ground layer yarns having substantially higher shrinkage capacity than the loop layer yarns 31, which can cause the loops 32 to be tightly held in the ground layer 20 when the fabric 10 is heated. In some embodiments, resilient recovery of the loops 32 to the non-compressed configuration 40 can be provided at least in part by each loop 32 being integrally knit into the ground layer 20, thereby providing tightly held loops 32 that tend to extend in an upright manner 42 away from the ground layer 20. In some embodiments, resilient recovery of the loops 32 to the non-compressed configuration 40 can be provided at least in part by the loops 32 being densely knit into the ground layer 20 so as to enhance the stability of the loops 32 in their outwardly extended position 42. In some embodiments, resilient recovery of the loops 32 to the non-compressed configuration 40 can be provided at least in part by thermoset memory of the fabric 10, as described herein.

The "point" 33 of the loop 32 is the portion of the loop 32 that is integrally knit into the ground layer 20. The "apex" 34 of the loop 32 is the portion opposite the point 33 of the loop 32 that extends outwardly away from the ground layer 20.

Due to the resilient recovery property of embodiments of the fabric 10 of the present invention, each loop 32 can stand up by itself from its point 33 knitted to the ground layer 20. Accordingly, in the non-compressed configuration 40, the dense, extended loops 32 in the loop layer 30 of the fabric 10 can provide a consistent height 43 and contour. In this manner, the loop layer 30 can have a consistent contact with the interior wall of a vessel, duct, or other anatomical structure along the length and width of the fabric 10. Such consistent contact with an adjacent vessel, duct, or other anatomical structure can enhance clotting and prevention of fluid flow between the exterior of an implanted device 50 such as the stent 53 and the vessel, duct, or other anatomical structure.

In some embodiments, the loop layer yarn 31 can comprise a multifilament yarn 31 having a high denier per filament ratio. "Multifilament" is defined as a manufactured fiber yarn composed of many fine filaments. Multifilament yarn 31 is desirable in some embodiments of the present invention due to the greater surface area exposed to a target location provided by multiple filaments in the yarn 31. In applications in which the fabric 10 is utilized in vascular implantation, for example, the multifilament loop yarn 31 can promote enhanced cellular ingrowth and encapsulation to promote clotting and fixation of the fabric 10 to a vessel wall. Lower denier filament yarns, such as those used in conventional medical textiles, provide increased surface area but generally fail to exhibit sufficient recovery or resiliency from compression (due to limited memory retention) to provide optimal sealing between an implantable device and an adjacent anatomical structure, such as a vessel wall.

The stability and resilience of the fabric 10, and in particular the loops 32, can be related to the denier per filament ratio (dpf) in the multifilament loop yarn 31. "Denier" is defined as the weight per unit length of yarn. Denier is numerically equal to the weight, in grams, of 9,000 meters length of yarn. The lower the denier, the lighter and finer the yarn. The higher the denier, the heavier and more coarse the yarn. "Denier per filament" (dpf) is defined as the size of each filament in a multifilament yarn equal to the total yarn denier divided by the number of filaments. The lower the dpf ratio, the harder it is for the loops 32 to spring back to their original configuration 40. Conversely, the higher the dpf ratio, the easier it is for the loops 32 to recover to the non-compressed configuration 40. Conventional medical device fabrics may comprise yarn having a total denier of about 150 and about 96 filaments, for a relatively low denier per filament (dpf) ratio of about 1.56.

In some embodiments of the compressible resilient fabric 10 of the present invention, the loop layer yarn 31 can have a total denier of about 60-70 denier and a relatively high denier per filament (dpf) ratio of about 5-20. That is, the denier per filament ratio in loop layer yarn 31 in the compressible resilient fabric 10 can be about 5-20 dpf, or about three to ten times greater, and the number of filaments can be about 40-50% less, than in conventional medical device fabric. In certain embodiments, the total denier for the loop yarn 31 in the compressible resilient fabric 10 can be less than about 60, for example, as low as about 10-15 denier, depending on the particular application for the fabric 10.

In addition to providing more stable loops 32 having greater resiliency, the higher denier per filament yarn 31 in the fabric 10 can provide loops 32 that are more compressible than conventional fabric having lower denier per filament yarn. It was discovered in experimentation that two layers of multifilament loop yarn 31 having a total denier of about 60-70 allows a compressed fabric thickness 45 of about 0.008 inches. This degree of compressibility was found to be sufficient for utilization in medical device applications. In addition, multifilament loop yarn 31 having a total denier of about 60-70 was found to provide sufficient resilience for the loops 32 to recover substantially their non-compressed configuration 40 having a thickness between about 1 mm and about 2 mm of when compression was relieved.

Fluid media may have an impact on resiliency and/or uniformity of resiliency of the fabric 10. Yarns having a relatively lower denier per filament ratio tend to absorb more fluid from fluid media in which they are packaged than yarns having a relatively high denier per filament ratio. Absorption of fluid from packaging media can cause the yarns to increase in volume, resulting in less resiliency when a compressive force is released from the fabric 10. Therefore, some embodiments of the compressible resilient fabric 10 of the present invention comprising high denier per filament yarn 31 may absorb less fluid from packaging media, and the resiliency of such fabric 10 may thus be less adversely affected by fluid media, than conventional medical device fabrics.

In some embodiments, yarn in the ground layer 20 can have heat shrinkage rates, or shrinkability, up to 40% to 60% of the length and width of the unprocessed ground layer 20. Such high rates of shrinkage in the yarn in the ground layer 20 can cause the courses and wales in the ground layer 20 to move closer together. In some embodiments, the yarns in the ground layer 20 can be under a higher tension than the yarns 31 in the loop layer 30. A tighter ground layer 20 can provide more densely positioned loops 32, thereby helping the loops 32 stand up and extend outwardly from the ground layer 20. As a result, the dense positioning of the loops 32 can help stabilize the loops 32. In this manner, the loops 32 can be securely positioned for consistent functionality after the compressible resilient fabric 10 is implanted within a patient and the fabric 10 is expanded to the non-compressed configuration 40. That is, when the compressive force is removed from the fabric 10, the loops 32 can recover, or resiliently reposition, to approximately their original, non-compressed height 43, which can be a substantially uniform height 43. Such a recoverable, substantially uniform loop layer height 43 can be particularly useful in medical applications in which a device may not completely conform to the contours of an anatomical structure in which it is implanted.

As described herein, the fabric 10 can be washed, dried, and heated during fabrication in order to shrink the high shrinkage ground layer yarn so as to cause the loop layer yarns 31 to stand up more effectively. A higher tension ground layer 20 can cause the loop points 33 to be tightly packed and the loop apices 34 to be at the greatest possible distance from the surface of the ground layer 20, thereby providing maximum loop height 43.

In particular embodiments, the loop yarn 31 can be a synthetic yarn, for example, a polyester yarn, with a heat shrinkage rate of between about 5% and about 8%. Maintaining the heat shrinkage rate of the loop yarn 31 in such a narrow range can provide shrinkage control of the loops 32 so that the compressibility, resilience, and other properties of the finished fabric 10 can be more consistent and predictable. Alternatively, a polyester yarn having a heat shrinkage rate in a broader range, such as between about 2% and about 10%, may be utilized for the loop yarn 31. When using such a yarn having a broader range of heat shrinkage rate, finish processing can be varied to control the compressibility, resilience, and other properties of the finished fabric.

Figure 4:
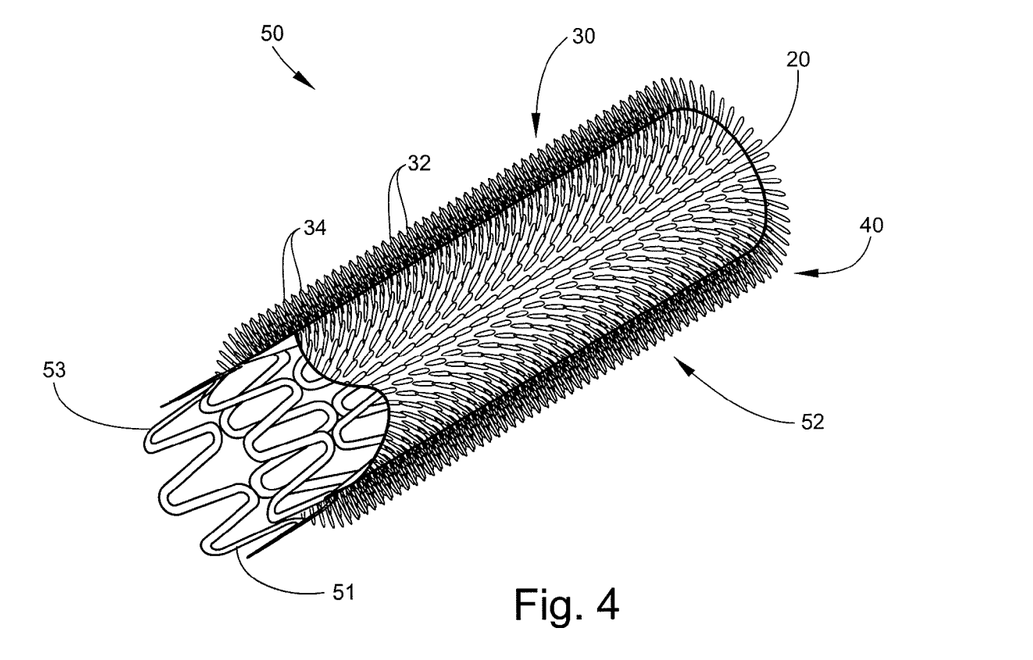
FIG. 4 is a diagrammatic perspective view of a partially cut-away intraluminal sealing member on the exterior of a stent in an embodiment of a device of the present invention.

Embodiments of the compressible resilient fabric 10 and/or device 50 can comprise various materials. Many synthetic materials can be utilized to promote thrombogenesis when implanted as an intraluminal sealing device 50. For example, nylon and/or polyolefins can serve as thrombogenic material(s) useful in the intraluminal sealing device 50. In certain embodiments, polyester may be utilized for the ground layer 20 and/or the loop layer 30 yarn(s) 31. In particular embodiments, different polyester yarns may be used in the ground layer 20 and loop layer 30. Polyester is known to be well-adapted for promoting tissue in-growth in and around the yarn.

In alternative embodiments, the compressible resilient fabric 10 can be fabricated with dissolvable materials. Such dissolvable materials can include, for example, polyglycolic acid (PGA) and/or ploylactide acid (PLA). Depending on the particular application, the compressible resilient fabric 10 can be fabricated with dissolvable materials alone or in combination with non-dissolvable materials, such as polyester.

In the compressed configuration 41, the fabric 10 can have a thickness 44 in the range of about 0.004-0.008 inches. Such a thin compressed configuration 41 can allow the fabric 10 to be easily inserted into a delivery catheter along with an intraluminal medical device, such as the device 50. The compressed thickness 44 of the fabric 10 can be affected by various factors, including, for example, the type of yarn, the porosity of the ground layer 20, and the density and height 43 of the loop layer 30.

For example, in the non-compressed, or expanded, configuration 40, the ground layer 20 can be very thin, for example, in the range of about 0.05-0.1 mm in height. The loops 32 can have a height 43 from the ground layer 20 of about 1-3 mm. In certain embodiments, the loop height 43 can be greater than 3 mm, depending on the size of the implantable device (for example the device 50) to which it is attached relative to the size and configuration of the vessel into which the device 50 is implanted. For example, if the design of the implantable device 50, such as the stent 53, is inserted into a particularly tortuous vessel and leaves a 4-5 mm gap between the exterior surface of the device 50 and the wall of the vessel into which it is implanted, the height 43 of the loops 32 can be 4-5 mm.

The compressibility and/or resiliency in the compressible resilient fabric 10 needed for particular applications can vary. For example, in some clinical situations, compressibility may be of greater concern in order to compress the fabric 10 or device 50 comprising such fabric 10 into a small enough delivery catheter to reach a target implant site. In other situations, resiliency may be a more important consideration for fuller recovery of the loops 32 to their non-compressed height 43 so as to provide a tighter seal between the device 50 and the vessel wall. That is, in some embodiments of the present invention, the fabric 10 can be constructed to provide an optimized balance between a sufficiently low number of loops 32 and/or height/density for adequate compressibility and a sufficiently high number of loops 32 and/or height/density for resilient recovery. Such balanced loop density and height 43 can be optimized for particular applications, for example, a heart valve or for a stent-graft for an aneurysm.

The compressibility and recovery of embodiments of the fabric 10 from the compressed configuration 41 to its substantially original non-compressed configuration 40 can be affected by a variety of factors. Such factors can include the type of yarn, the denier per filament of yarn, the fabric construction, and the method of fabrication, among others. For example, in some embodiments, the ground layer 20 can have a porosity that can provide some space into which the loops 32 can be compressed. In some embodiments, the loops 32 can be held tightly and/or densely packed on the ground layer 20. In some embodiments, the loops 32 can be sufficiently thin to allow packing in a compressed state and/or sufficiently thick to allow sealing with clots. In particular embodiments, the yarn in the ground layer 20 can comprise about two-thirds of the fabric volume, and the yarn 31 in the loops 32 can comprise about one-third of the fabric volume.

Some embodiments of the present invention can include a device 50, as shown in FIG. 4, comprising a substantially tubular inner member 51, and an intraluminal sealing member 52 attachable to the exterior of the inner member 51. In some embodiments, the inner member 51 can comprise an implantable medical device, for example, a stent 53. FIG. 3 illustrates a cross-section of the fabric 10 (or sealing member 52) in a tubular configuration, as may be applied to the inner member 51. The sealing member 52, or fabric 10, may be attached to the tubular inner member 51 using various techniques. For example, the sealing member 52, or fabric 10, may be attached to the tubular inner member 51 with an adhesive material, by stitching the sealing member 52, or fabric 10, to the inner member 51, or by other methods.

The sealing member 52 can include the ground layer 20 of knitted yarn and a loop layer 30 comprising a plurality of loops 32 of yarn 31, each loop 32 having a point 33 knit into the ground layer 20. The sealing member 52 can be compressible from a non-compressed configuration 40, in which each loop 32 has an apex 34 extending substantially perpendicularly and radially outward 42 from the ground layer 20, into a compressed configuration 41, in which each loop 32 is collapsed onto and/or into the ground layer 20. The sealing member 52 can be resilient so as to substantially resume the non-compressed configuration 40 when compression is relieved, for example, after the device 50 is implanted into a lumen in a human or animal body. The intraluminal sealing member 52 can be adapted to promote sealing between the inner member 52 and a lumen wall.

As shown in FIGS. 3 and 4, the implantable device 50 and the inner member 51 can be tubular in shape. Such tubular embodiments can be utilized in cardiovascular applications, such as with a heart valve or stent-graft. In such applications, the intraluminal sealing member 52 can be formed, wrapped, or attached about the radially expanding inner member 51. In this manner, when the device 50 is implanted in a target location, flow of blood between the exterior of the device 50 and the wall of the vessel can be restricted and/or prevented. When the device 50 is radially expanded, there can be gaps and/or voids between the implanted device 50 and the vessel wall because the flexibility of the device 50 may not completely conform to the contours of the vessel. The intraluminal sealing member 52 can fill those gaps and/or voids. Accordingly, the sealing member 51, and/or fabric 10, can function as an in vivo sealant or gasket for the expandable medical device 50. In certain embodiments, the loops 32 can comprise a thrombogenic material, such as polyester, that can further enhance clotting by the sealing member 52, or fabric 10. In addition, the intraluminal sealing member 52 can serve as a frictional retention mechanism to help secure the implanted device 50 to the target location in the body.

In some embodiments of such a device 50, the loop layer yarn 31 can comprise a high denier per filament multifilament yarn 31. For example, the multifilament yarn 31 in the device 50 can have 5-20 denier per filament. In some embodiments, the loop layer yarn can comprise a total denier of 60-70. The high denier per filament yarn 31 can enhance the ability of the loops 32 to stand upright so as to extend substantially perpendicularly outward 42 from the ground layer 20. Such structural support within the loops 32 can provide enhanced stability to the loops 32 to maintain their upright positioning 42. In certain embodiments, each loop 32 can have a substantially uniform height 43 in the non-compressed configuration 40. As a result, the loop layer 30 of the intraluminal sealing member 52 can provide a consistent contact, and thus a reliable seal, between the underlying tubular inner member 51 and the wall of a lumen into which it is implanted.

In some embodiments, the ground layer yarn of the intraluminal sealing member 52 can comprise a yarn that is substantially more shrinkable than the loop layer yarn 31. For example, the ground layer 20 may comprise a yarn shrinkable about 40-60%, and the loop layer 30 may comprise a yarn 31 shrinkable about 5-8%. The loop yarn 31 and/or the ground yarn can comprise various yarns. A particularly useful type of yarn in either or both layers 20, 30, respectively, is a polyester yarn. The polyester yarn can be different in each of the ground and loop layers 20, 30, respectively.

In some embodiments of such a device, the loops in the intraluminal sealing member can be densely knit to further enhance the upright stability of the loop layer. For example, the loop layer can include two loops knit in every four courses of the ground layer. In certain embodiments, the loop layer can include between about 600 and 750 loops per square inch of the fabric.

In some embodiments of such a device 50, the intraluminal sealing member 52 can be compressed from the non-compressed configuration 40 to the compressed configuration 41. In the non-compressed configuration 40, some embodiments of the sealing member 52 can have a thickness of about 1-5 mm. In the compressed configuration 41, some embodiments of the sealing member 52 can have a thickness of about 0.004-0.008 inches.

In some embodiments of the present invention, the multifilament loops 32 can promote clot formation within the loops 32. A typical clotting cascade can occur in which blood clots form first on the inside of the loops 32 and then progressively outwardly until a clot forms a solid connection between the fabric 10 and/or sealing member 52 and the adjacent anatomical structure, such as a vessel wall. In this way, the clot facilitated by the loop structure and size can help secure the fabric 10 and/or device 50 in place and prevent blood flow around the outside of the device 50. The height of the loops 32 can vary, depending on the underlying device 50, the target location for implantation, and the degree of loop compressibility desired. A greater height of the loops 32 provides a larger surface area for clot formation and can minimize dislodgement of the forming clots. An optimal loop height 43 can allow promotion of clot formation while allowing sufficient compressibility of the loops 32.

In some embodiments, movement and positioning of the compressible resilient fabric 10 and/or device 50 can be monitored fluoroscopically or under CT visualization. For example, the compressible resilient fabric 10 can include radiopaque material such that positioning and expansion of the device 50 and the attached fabric 10 can be monitored. Radiopaque is defined as being opaque to radiation and especially x-rays. In certain embodiments, a plurality of radiographic markers (not shown) can be in communication with predetermined portions of the compressible resilient fabric 10 and/or implantable device 50 so that when the device 50 moves, movement and positioning of the markers—and the fabric 10 and/or device 50 in communication therewith—can be visualized.

Embodiments of the compressible resilient fabric 10, device 50, system, kit, and method as described herein can be utilized in medical applications, including, for example, in vascular and endovascular implants such as stents, stent-grafts, and heart valves. Some embodiments may be applicable for use in various other types of anatomical structures and locations, for example, in shunts between organs and/or in gastrointestinal, pulmonary, neurological, and/or other structures and locations of a human or animal body.

Embodiments of the compressible resilient fabric 10 and/or device 50 can have advantages over conventional fabrics and devices. For example, one advantage is that the fabric 10 and/or sealing member 52 can be sufficiently compressible for inserting into a target location and sufficiently resilient to recover to substantially its non-compressed configuration 40 when in the target location and the compression is relieved. As a result, the fabric 10 and/or sealing member 52 are adapted to promote sealing between the fabric 10 and/or sealing member 52 and an adjacent anatomical structure, such as a lumen wall. In certain embodiments, the compressible resilient fabric 10 and/or device 50 can provide frictional contact between the fabric 10 or device 50 and the adjacent anatomical structure. Such a frictional contact can help prevent blood flow around the fabric 10 and/or device 50 and provide a surface for clot formation to further secure the fabric 10 and/or device 50 in the desired implant position.

Another advantage of some embodiments of the compressible resilient fabric 10 and/or device 50 is that the loops 32 can have sufficient stability in the perpendicularly extended (upright) position 42 relative to the ground layer 20 to provide a uniform loop height 43, and thereby consistent contact with an adjacent anatomical structure. Loop stability can be advantageously provided by various aspects of embodiments of the present invention. For example, the loops 32 can be stabilized in the outwardly extended position 42 by each loop 32 being integrally knit into the ground layer 20, by knitting the loops 32 closely together in a dense pattern, by high denier per filament yarn 31 in the loops 32, and by the ground yarn having a high shrinkage capacity that when shrunk causes the loops 32 to become more tightly packed.

Another advantage of some embodiments of the compressible resilient fabric 10 and/or device 50 is that loops comprising high denier per filament yarn can retain resiliency when stored in fluid media.

Some embodiments of the present invention can include a system and/or kit. Such a system and/or kit can include a compressible resilient fabric 10 and/or devices 50 including a compressible resilient fabric 10 as described herein. For example, some embodiments of such a system and/or kit can include the fabric 10 and/or intraluminal sealing member 52 comprising a ground layer 20 of knitted yarn, and a loop layer 30 comprising a plurality of loops 32 of yarn 31, each loop 32 having a point 33 knit into the ground layer 20. The fabric 10 and/or intraluminal sealing member 52 can be compressible from an non-compressed configuration 40, in which each loop 32 has an apex 34 extending substantially perpendicularly outward 42 from the ground layer 20, into the compressed configuration 41, in which each loop 32 is collapsed onto the ground layer 20. The fabric 10 can be resilient so as to substantially resume the non-compressed configuration 40 when compression is relieved.

The loops 32 in embodiments of the fabric 10 and/or intraluminal sealing member 52 can be stabilized in the outwardly extended position 42 by various means, including by each loop 32 being integrally knit into the ground layer 20, by knitting the loops 32 closely together in a dense pattern, by high denier per filament yarn 31 in the loops 32, and by the ground yarn having a high shrinkage capacity that when shrunk causes the loops 32 to become more tightly packed.

The system and/or kit may further comprise additional components, for example, a delivery catheter for a device that includes the fabric 10 and/or intraluminal sealing member 52.

Some embodiments of the present invention can include a method of making a compressible resilient fabric 10 and/or devices 50 including the compressible resilient fabric 10 as described herein. For example, one such a method can include knitting the ground layer 20 of yarn and the loop layer 30 comprising a plurality of loops 32 of yarn 31, each loop 32 having a point 33 knit into the ground layer 20. In the fabric 20 and/or device 50 made by such a method, the fabric 10 can be compressible from the non-compressed configuration 40, in which each loop 32 has an apex 34 extending substantially perpendicularly outward 42 from the ground layer 20, into the compressed configuration 41, in which each loop 32 is collapsed onto the ground layer 20. The fabric 10 can further be resilient so as to substantially resume the non-compressed configuration 40 when compression is relieved. In some embodiments of a method, the loop layer 30 can be knit with a multifilament yarn 31 having 5-20 denier per filament and a total denier of 60-70. A high denier per filament yarn can increase the extensibility and stability of loop positioning.

Embodiments of the compressible resilient fabric 10 and/or intraluminal sealing member 52 of the present invention can be made utilizing warp knitting techniques, for example, on a double-bar raschel knitting machine. As used herein, "warp knitting" is defined as a method of knitting fabric out of one or more sets of yarn prepared as warps on beams. The yarns are fed through one or more guide bars to knitting needles that form the yarns into interlaced loops 32. The guide bars move the yarns around the needles and from needle to needle to create the warp knit fabric. In warp knitting, there is simultaneous yarn-feeding and loop-forming action occurring at every needle in the guide bar during the knitting cycle. All needles in the needle bar are simultaneously lapped by separate guide bars. A "warp knit fabric" is a knit fabric in which the yarns generally run lengthwise but in a zigzag patterns, which forms loops 32 in two or more wales.

In one alternative warp knitting technique to form the high pile fabric 10, a "dummy needle" can be used to fill a needle space on a knitting machine when no needle is required for the pattern. In another alternative warp knitting technique, yarn ends can be looped around a pole to help form a loop 32 into a particular size. Use of a "pole" or pile sinker can be helpful for knitting relatively larger loops 32.

Warp knitting can be advantageous for making the compressible resilient fabric 10 and/or intraluminal sealing member 52 in that warp knitting decreases the risk of the fabric 10 or sealing member 52 from fraying and from unraveling when cut. Warp knitting provides a manufacturing process that can result in consistent quality of knitted products.

In some embodiments of the compressible resilient fabric 10 and/or intraluminal sealing member 52, the loops 32 can be integrally knit with the ground layer 20 utilizing a stitch design that ensures the points 33 of the loops 32 are held tightly to the ground layer 20. Such tight loop layer 30—ground layer 20 knitting can help the loops 32 stand upright 42 away from the ground layer 20 surface, thereby contributing to the resilience of the loops 32.

Figure 5:
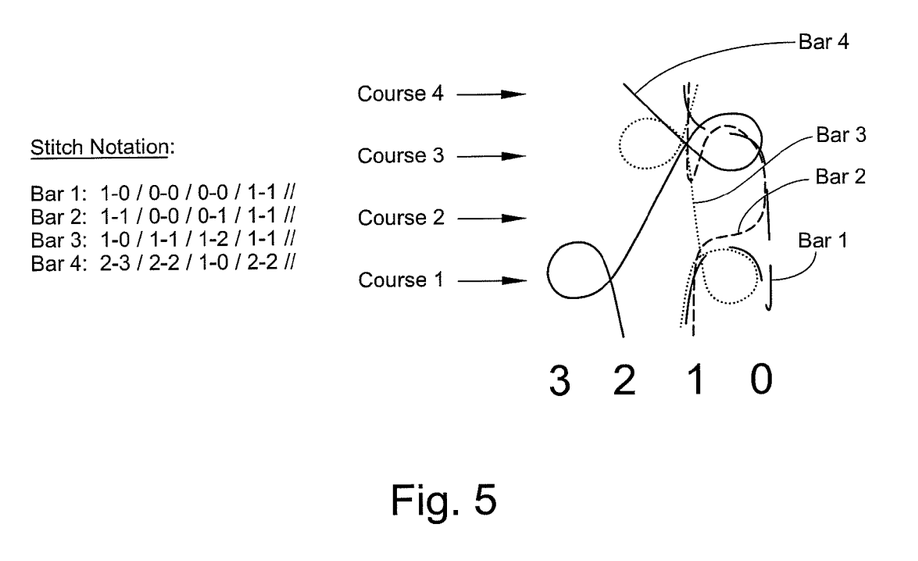
FIG. 5 is a view of a knitting stitch diagram of one four-course repeat for a compressible resilient fabric showing two loops in four courses in an embodiment of the present invention.

FIG. 5 shows a knitting stitch diagram of one four-course repeat for one exemplary embodiment of the compressible resilient fabric 10. The 3-2-1-0 designation in FIG. 5 represents spaces between needles along the direction of the wales in the fabric 10. Courses 1-4 are indicated along the left hand side of the diagram. In this knitting pattern, four guide bars (bars 1-4) alternate between two needle beds. While bars 3 and 4 knit in their respective courses, bars 1 and 2 each knit once in every four-course repeat. Thus, bars 1 and 2 produce open stitch loops 32 in alternating courses, providing two loops 32 in every four course repeat. The stitch notation in FIG. 5 designates the path of the yarn on each bar between the needles. For example, the yarn on bar 1 travels in course 1 starting in space 1 and forms loop ending in space 0; stays in space 0 in courses 2 and 3; and then moves to space 1 in course 4. Since the yarn stays in the same space (space 0) in courses 2 and 3, an open stitch loop 32 is formed.

In some embodiments, selected guide bars from which the ground layer 20 is knit can be tightly spaced so as to knit the ground layer 20 more tightly to create a more densely packed loop layer 30. In some embodiments of a method, the loop layer 30 can be knit having between about 600 and about 750 loops 32 per square inch of the fabric 10.

Another embodiment of a method of making the compressible resilient fabric 10 and/or devices 50 can include pile knitting. In a pile knitted construction, the pile (for example, loops 32) stand out substantially at right angles 42 from the technical back of the knitted ground layer 20. As used herein, "pile" refers to yarns (for example, loops 32) that stand away, or extend outwardly 42, from the surface of the fabric 10. Sinker loops or underlaps can be used to produce this effect. Such a technique can be varied by using a double needle bar knitting machine, and pressing off on the second set of needles to produce the pile surface layer. Point or looped pile can be produced on a double-bar raschel knitting machine by replacing the front bar needles by a point or pin bar around which the pile yarns are overlapped. Pile knitting can produce a high pile fabric that has resistance to unraveling similar to the ravel-resistance achievable with warp knitting. A pile knitting machine also has the ability to hold slack in a stitch to create the ground layer 20 having higher tension than the loops 32, thereby further enhancing the stability of the extended loops 32. Pile knitting can provide for variation in the size of the loops 32, which can be customized by changing the size of the knitting elements.

Knitted constructions of the compressible resilient fabric 10 can provide loops 32 having greater extensibility than in other construction modalities, such as weaving. Enhanced loop extensibility can allow greater height 43 of the loops 32 and thus greater contact with a vessel wall and more surface area for blood to clot between the exterior surface of a device 50 to which the fabric 10 is attached and the interior wall of the vessel into which the device 50 is implanted. Knitting also offers the advantage of providing enhanced stretch and recovery, or resiliency, of the loops 32. In addition, warp knitting can provide a more flexible process for making a tubular device 50 with the fabric 10, while still providing for the fabrication of the ground layer 20 and the loop layer 30.

Although knitting may be a preferred technique for making some embodiments of the compressible resilient fabric 10, the fabric 10 can also be made by weaving. Weaving may be utilized to produce a high pile fabric having a highly stable ground layer 20. In addition, a thinner and more flexible fabric 10 may be made by weaving, which can facilitate production of a tubular device 50. In woven embodiments of the fabric 10, the loops 32 can comprise floated yarns. Thus, woven embodiments of the present invention may provide the advantages of increased stability, while including a thinner fabric 10.

Some embodiments of a method of making the compressible fabric 10 and/or intraluminal sealing member 52 can further include washing the fabric 10 or sealing member 52 in about 90 degree C. water. Washing the fabric 10 or sealing member 52 after formation can advantageously cause some shrinkage of the fabric 10 or sealing member 52. It may be desirable to place the fabric 10 or sealing member 52 inside a protective housing such as a mesh covering or bag to protect the loops 32 from rigorous agitation or disturbance during washing. The wash can include use of detergent(s), softener(s), and/or other additives.

After washing, the fabric 10 or sealing member 52 can be dried at about 60-65 degrees C. The fabric 10 or sealing member 52 can be dried in a tumble dryer. Drying at this temperature can cause the fabric 10 or sealing member 52 to shrink further. The ground layer 20 and the loop layer 30 can each be knit with a yarn(s) having a different degree of shrinkability. For example, the ground layer yarn can be substantially more shrinkable than the loop layer yarn 31. In one particular embodiment, washing and drying the fabric 10 and/or intraluminal sealing member 52 can shrink the ground layer 20 about 40-60% and shrink the loop layer 30 about 7-8%.

After the washing and drying processes, the fabric 10 or sealing member 52 can be thermoset in a dry oven. Such heat-setting can improve the memory of the fibers in at least the loop layer yarns 31. In addition, heat-setting can create pockets in the ground layer 20 that allow the loops 32 to be compressed into areas within the ground layer 20, resulting in a thinner fabric in the compressed configuration 41.

Certain embodiments of a method of making the fabric 10 or sealing member 52 can further include stretching the fabric 10 or sealing member 52 in the width or course-wise direction prior to drying the fabric 10 or sealing member 52 so as to heat set the fabric 10 or sealing member 52 under tension. For example, in some embodiments, each of the yarn ends of the fabric 10 or sealing member 52 can be releasably attached to pins in a pin frame. The pins in the pin frame can secure the edges of the fabric 10 or sealing member 52 to stabilize the fabric 10 or sealing member 52 with an even tension throughout the fabric 10 or sealing member 52 in order to achieve a consistent degree of final shrinkage as the fabric 10 or sealing member 52 is being heat set. Stretching the fabric 10 or sealing member 52 in the heat-setting process can thus provide a desired orientation for memory by the fabric 10 or sealing member 52 once heat set.

Some embodiments of the present invention can include a method of using the compressible resilient fabric 10 and/or devices 50 including the compressible resilient fabric 10 as described herein. For example, one such a method can include utilizing the device 50 comprising the substantially tubular inner member 51, such as the stent 53, and the intraluminal sealing member 52 attachable to the exterior of the inner member 51. The sealing member 52 can include the ground layer 20 of knitted yarn and the loop layer 30 comprising a plurality of loops 32 of yarn 31, each loop 32 having a point 33 knit into the ground layer 20. The sealing member 52 can be compressed from the non-compressed configuration 40, in which each loop 32 has an apex 34 extending substantially perpendicularly and radially outward 42 from the ground layer 20, into the compressed configuration 41, in which each loop 32 is collapsed onto the ground layer 20. After the device 50 is implanted into a lumen in a human or animal body and compression is relieved, the sealing member 52 can recover so as to substantially resume its non-compressed configuration 40. The intraluminal sealing member 52 can be adapted to promote sealing between the inner member 51 and a lumen wall.

Although the present invention has been described with reference to particular embodiments, it should be recognized that these embodiments are merely illustrative of the principles of the present invention. Those of ordinary skill in the art will appreciate that a compressible resilient fabric 10, device 50, system, kit, and methods of the present invention may be constructed and implemented in other ways and embodiments. Accordingly, the description herein should not be read as limiting the present invention, as other embodiments also fall within the scope of the present invention.

What is claimed is:

1. A fabric, comprising:
    a ground layer of knitted yarn; and
    a loop layer comprising a plurality of loops of yarn, each loop having a point knit into the ground layer,
    wherein the fabric is compressible from a non-compressed configuration, in which each loop has an apex extending substantially perpendicularly outward from the ground layer, into a compressed configuration comprising a thickness of about 0.004-0.008 inches and in which each loop is collapsed onto the ground layer, and
    wherein the fabric is resilient so as to substantially resume the non-compressed configuration by returning the loops to approximately an original, non-compressed height when compression is relieved.

2. The fabric of claim 1, wherein the ground layer yarn comprises a yarn shrinkable substantially more than the loop layer yarn.

3. The fabric of claim 1, wherein the ground layer yarn comprises a yarn having a higher shrinkability than the loop layer yarn.

4. The fabric of claim 1, wherein the loop layer further comprises two loops in every four courses of the ground layer.

5. The fabric of claim 1, wherein the loop layer further comprises between about 600 and about 750 loops per square inch of the fabric.

6. The fabric of claim 1, wherein each loop further comprises a substantially uniform height in the non-compressed configuration.

7. The fabric of claim 1, wherein the fabric further comprises a thickness of about 1-5 mm in the non-compressed configuration.

8. The fabric of claim 1, wherein at least the loop yarn further comprises a polyester yarn.

9. The fabric of claim 1, wherein the loop layer yarn comprises a multifilament yarn having 5-20 denier per filament.

10. The fabric of claim 1, wherein the ground layer comprises a porosity sufficient to allow collapse of each loop onto the ground layer.

11. A fabric, comprising:
   a ground layer of knitted yarn; and
   a loop layer comprising a plurality of loops of multifilament yarn having a total denier of about 60-70, each loop having a point knit into the ground layer,
   wherein the fabric is compressible from a non-compressed configuration, in which each loop has an apex extending substantially perpendicularly outward from the ground layer, into a compressed configuration comprising a thickness of about 0.008 inches and in which each loop is collapsed onto the ground layer, and
   wherein the fabric is resilient so as to substantially resume the non-compressed configuration having a thickness between about 1 mm and about 2 mm by returning the loops to approximately an original, non-compressed height when compression is relieved.

* * * * *